United States Patent [19]

Lechtken et al.

[11] Patent Number: 4,925,960

[45] Date of Patent: May 15, 1990

[54] PREPARATION OF D-α-TOCOPHEROL FROM NATURAL INTERMEDIATES

[75] Inventors: Peter Lechtken, Frankenthal; Ulrich Hoercher, Mannheim; Barbara Jessel, Ludwigshafen, all of Fed. Rep. of Germany

[73] Assignee: BASF Aktiengesellschaft, Ludwigshafen, Fed. Rep. of Germany

[21] Appl. No.: 337,840

[22] Filed: Apr. 13, 1989

[30] Foreign Application Priority Data

Apr. 22, 1988 [DE] Fed. Rep. of Germany ....... 3813624

[51] Int. Cl.⁵ .......................................... C07D 311/72
[52] U.S. Cl. .................................................. 549/412
[58] Field of Search .......................................... 549/412

[56] References Cited

U.S. PATENT DOCUMENTS

| | | | |
|---|---|---|---|
| 2,486,539 | 11/1949 | Weisler et al. | 549/412 |
| 2,486,542 | 11/1949 | Weisler et al. | 549/412 |
| 2,843,604 | 7/1958 | Hawks et al. | 549/412 |
| 3,819,657 | 6/1974 | Baldwin et al. | 549/412 |
| 4,239,691 | 12/1980 | Nelan et al. | |

FOREIGN PATENT DOCUMENTS 178400 7/1985 European Pat. Off.
2351272 10/1973 Fed. Rep. of Germany.

OTHER PUBLICATIONS

Reinhold Plastics Application Series, Reinhold Publishing Corp., U.S.A.–1959 "Phenolic Resins", p. 26 and table on p. 28.

Primary Examiner—Nicky Chan
Attorney, Agent, or Firm—Oblon, Spivak, McClelland, Maier & Neustadt

[57] ABSTRACT d-α-Tocopherol is prepared from a mixture obtained from natural intermediates and containing α-, β-, γ- and δ-tocopherols, by methylation at the aromatic ring of the tocopherols by reaction with formaldehyde or with a compound which donates formaldehyde under the reaction conditions, and subsequent catalytic hydrogenation, by a process in which the reaction with formaldehyde or with the formaldehyde donor is carried out at from 150° to 200° C. in the presence of an alkyl ester of phosphoric or phosphorous acid.

7 Claims, No Drawings

PREPARATION OF D-α-TOCOPHEROL FROM NATURAL INTERMEDIATES

The present invention relates to a process for the preparation of d-α-tocopherol from a mixture obtained from natural intermediates and containing α-, β-, γ- and δ-tocopherols, by methylation of the tocopherols at the aromatic ring by reaction with formaldehyde and catalytic hydrogenation.

Naturally occurring vitamin E is a mixture of α-, β-, γ- and δ-tocopherol, which is stereochemically pure, having all chiral centers in the R form. α-, β-, γ- and δ-forms differ merely in the degree of methylation at the benzene ring:

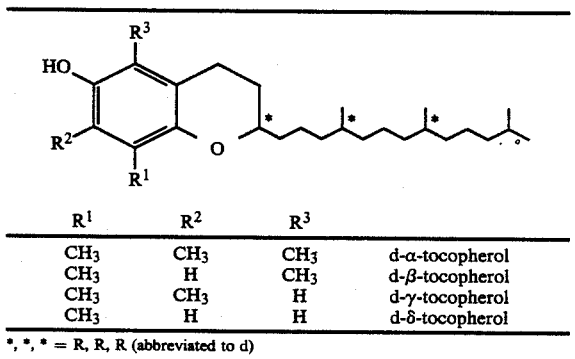

| R¹ | R² | R³ | |
|---|---|---|---|
| CH₃ | CH₃ | CH₃ | d-α-tocopherol |
| CH₃ | H | CH₃ | d-β-tocopherol |
| CH₃ | CH₃ | H | d-γ-tocopherol |
| CH₃ | H | H | d-δ-tocopherol |

*, *, * = R, R, R (abbreviated to d)

The various tocopherols have different vitamin E potencies. d-α-tocopherol has by far the highest potency and is thus the most important product.

Synthetic methods for the preparation of the optically pure d-α-tocopherol have so far proven uneconomical. It has therefore been necessary to isolate the substance from natural materials. Particularly suitable natural intermediates are vegetable fats and oils which are rich in tocopherols, such as soybean oil, sunflower oil, rape oil, palm oil, cotton-seed oil, linseed oil, coconut oil and wheatgerm oil.

The deodorizer condensate which is obtained in the steam deodorization of edible oils and contains 4–15% of tocopherols is particularly preferred.

Since these natural tocopherols generally only contain a small amount of the highly potent d-α-tocopherol and predominantly consist of d-β-, d-γ- and d-δ-tocopherols (ie. non-α-tocopherols), it is an object of the present invention to provide a process which can be carried out in a commercially acceptable manner, avoids very toxic chemicals and gives stereochemically pure d-α-tocopherol in high yield.

Some processes for the conversion of non-α-tocopherols into α-tocopherol have been described. An example is chloromethylation with formaldehyde and HCl and subsequent reduction of the chloromethyl group to the methyl group by means of SnCl₂, metallic zinc or hydrogen in the presence of Ni or Pd (cf. U.S. Pat. Nos. 2,486,539, 2,486,542 and 2,843,604). In these methods, however, there is a danger that the carcinogenic chlorodimethyl ether will be formed. Another disadvantage of these processes is the pollution of the waste-water by heavy metals.

The conversion of non-α-tocopherols with formaldehyde in the presence of acids, such as orthophosphoric acid (cf. DE 2 351 272), strongly acidic ion exchangers (cf. U.S. Pat. No. 4,239,691 or EP-A 178 400) or acetic acid (cf. Japanese Preliminary Published Application 56-68677), and subsequent hydrogenation has also been disclosed.

However, these processes too are not completely satisfactory since the acids used in the hydroxymethylation cause partial racemization at the center of chirality in the chroman ring and the object of preparing only the naturally occurring, optically pure, R,R,R-tocopherol is thus not fully achieved.

Furthermore, the strong acids result in corrosion problems and hence contamination of the tocopherol with heavy metals, and these problems can only be solved by using very expensive special steels as plant material.

It is an object of the present invention to improve the basically advantageous process for the conversion of non-α-tocopherols into α-tocopherols by hydroxymethylation with formaldehyde and subsequent catalytic hydrogenation, in such a way that the racemization at the center of chirality of the chroman ring is very greatly reduced and there are no significant corrosion problems even when conventional steels are used.

We have found that this object is achieved and that, surprisingly, d-α-tocopherol can be prepared in high yields from natural mixtures of α-, β-, γ- and δ-tocopherols if the hydroxymethylation at the benzene ring of the non-α-tocopherols is carried out by means of formaldehyde in the presence of an ester of phosphoric acid or of phosphorous acid.

The present invention accordingly relates to a process for the preparation of d-α-tocopherol from a mixture obtained from natural intermediates and containing α-, β-, γ- and δ-tocopherols, by methylation at the aromatic ring of the tocopherols by reaction with formaldehyde or a compound which donates formaldehyde under the reaction conditions, and subsequent catalytic hydrogenation, wherein the reaction with formaldehyde or with the formaldehyde donor is carried out at from 150° to 200° C. in the presence of an alkyl ester of phosphoric acid or of phosphorous acid.

While a number of strongly acidic or strongly alkaline catalysts are known for the reaction of formaldehyde with phenols (cf. for example Phenolic Resins by D. F. Gould, Reinhold Plastics Application Series, Reinhold Publishing Corporation, USA 1959, page 26 and Table on page 28), the novel process has made it possible for the first time to use a neutral catalyst, ie. an ester of phosphoric acid or of phosphorous acid, for the hydroxymethylation with formaldehyde.

This process gives d-α-tocopherol in yields of about 90%, racemization at the C-2 atom being negligible (≦2%) and vessel material resistance being good.

Suitable esters of phosphorous acid or of phosphoric acid are commercial alkyl esters, in particular those which are derived from straight-chain, branched or isoalcohols of 1 to 6 carbon atoms, and these alkyl radicals may be identical or different. Particular examples are trimethyl phosphate and triethyl phosphate.

The amount of phosphorous or phosphoric acid ester to be used is from 5 to 200%, particularly preferably from 10 to 50%, based on tocopherol mixture used.

The formaldehyde can be used as gaseous formaldehyde or in the form of its aqueous solution (formalin) but is preferably employed in the form of a formaldehyde donor, such as its anhydrous oligomers or polymers, such as trioxane, metaldehyde or paraformaldehyde.

The reaction is particularly advantageously carried out using formaldehyde or the formaldehyde donor in a $C_1$–$C_3$-alkanol or in methyl acetate or ethyl acetate.

In a particularly advantageous novel conversion of the non-α-tocopherols into α-tocopherol, the reaction with formaldehyde and the catalytic hydrogenation are carried out together, more or less simultaneously, in a pressure vessel. Temperatures of from 150° to 220° C. have proven particularly suitable. The hydrogenation takes place even at low hydrogen pressures. In general, hydrogen pressures of from 20 to 150, preferably from 30 to 100, bar are employed.

If the hydrogenation is carried out separately from the hydroxymethylation, it can be effected at as low as room temperature.

The hydrogenation catalysts used are in general the conventional noble metal catalysts, such as palladium and platinum, in pure form, as a supported catalyst or as a compound such as $PtO_2$. Pd on active carbon, containing from 5 to 10% of Pd, has proven particularly suitable for the novel reaction. However, other metals, such as nickel and Raney nickel, can also be used.

Advantageously used solvents are $C_1$–$C_3$-alkanols and methyl acetate or ethyl acetate.

A preferred embodiment of the novel process comprises a quasi-continuous procedure in which the hydrogenation catalyst is initially taken in a pressure vessel and the reactants are combined at the reaction temperature under hydrogen pressure in the pressure vessel. After the reaction, the reaction vessel is emptied via a frit at the reaction temperature or at a slightly lower temperature. The catalyst remains in the autoclave, and can be reused after washing with methanol.

By means of the novel process, d-α-tocopherol can be prepared from a mixture obtained from natural intermediates and containing α-, β-, γ- and δ-tocopherols, by methylation at the aromatic ring of the tocopherols by reaction with formaldehyde and catalytic hydrogenation, in good yields, even when the neutral catalysts are used, with the result that racemization and corrosion problems can be avoided.

The Examples which follow illustrate the novel procedure without limiting it.

EXAMPLE 1

80 g of a natural mixture of tocopherols which is obtained from deodorizer condensate and contains 4.0% of α-, 1.3% of β-, 54.8% of γ- and 40.6% of δ-tocopherol were introduced into a 1.2 l autoclave, together with 240 g of methanol, 1.12 g of 10% Pd/C, 29.8 g of paraformaldehyde and 25.2 g of trimethyl phosphate. The autoclave was closed and then flushed twice with $N_2$, after which hydrogen was forced in under a pressure of 30 bar and the mixture was heated to 200° C. in the course of 1 hour (h). The resulting pressure was about 80 bar. After 5 h, the autoclave was cooled, the autoclave content was washed out with n-hexane and the catalyst was filtered off. The hexane phase was extracted three times with 250 ml of $H_2O$, and the aqueous phase was washed once with hexane. The methanol phase was mixed with the same amount of water, and the resulting oil phase was removed and evaporated down together with the hexane phase in a rotary evaporator under 0.3 mm and at 60° C. 71.5 g of a brownish oil consisting of 95.3% of α-tocopherol and only 0.3% of β-, 1.15% of γ- and 0.15% of δ-tocopherol were obtained.

Gas chromatographic analysis (cf. Noal Cohen et al. Helv. Chim. Acta 64 (4) (1981), 1158–1173) furthermore indicated that the α-tocopherol obtained consisted of 98.4% of RRR- and only 1.6% of SRR-α-tocopherol.

EXAMPLE 2

Comparative Example 80 g of the natural tocopherol mixture described, consisting of α-, β-, γ- and δ-tocopherol, were introduced into a 1.2 l autoclave together with 240 g of methanol, 29.8 g of paraformaldehyde, 1.12 g of 10% Pd/C and 12.8 g of $P_2O_5$, the procedure described in Example 1 being used. After flushing with $N_2$, hydrogen was forced in under 30 bar at room temperature and the mixture was heated to 200° C. in the course of 1 h. After 5 h, the autoclave was cooled, the autoclave content was washed out with n-hexane, the catalyst was filtered off under suction and the reacted mixture was worked up similarly to Example 1.

78.4 g of a brownish oil which consisted of 9.23% of α-tocopherol and 0.57% of β-, 2.63% of γ- and 0.21% of δ-tocopherol were obtained.

Gas chromatographic analysis showed that the α-tocopherol consisted of 94.1% of RRR- and 5.9% of SRR-α-tocopherol.

This Comparative Example shows that racemization is substantially more pronounced when strongly acidic catalysts are used than in the novel reaction in the presence of neutral phosphoric esters (cf. Example 1).

EXAMPLE 3

Comparison of the Novel Reaction Using a Neutral Catalyst with the known Reaction over the strongly acidic catalyst $P_2O_5$ 11.3 g of a natural tocopherol mixture obtained from soybean oil and containing 5.68% of α-, 1.31% of β-, 42.75% of γ- and 38.87% of δ-tocopherol were introduced, together with 10 g of trioxane, 60 g of methanol and 0.56 g of 10% Pd/C, into each of two miniautoclaves (M1 and M2) having a capacity of 300 ml.

Miniautoclave M1 was charged with 6.3 g of triethyl phosphate, whereas miniautoclave M2 was charged with 3.2 g of $P_2O_5$ as catalyst.

After each autoclave had been closed and flushed with $N_2$, hydrogen was forced in under 50 bar, and each autoclave was heated to 200° C. while stirring (stirrer speed about 800 rpm) and kept at this temperature for 5 h.

Thereafter, each autoclave was allowed to cool, the contents were taken up in ethanol and the resulting tocopherol mixture was assayed by means of HPLC.

The reactions achieved for six successive runs are shown in Table 1. It was found that triethyl phosphate leads to roughly the same yields and conversions as $P_2O_5$.

TABLE 1

| | Tocopherols in the reacted mixture (%) | | | | |
|---|---|---|---|---|---|
| | Autoclave | Alpha | Beta | Gamma | Delta |
| a | M 1 | 98.18 | — | — | — |
| | M 2 | 99.41 | — | — | — |
| b | M 1 | 99.48 | — | — | — |
| | M 2 | 99.35 | — | — | — |
| c | M 1 | 99.66 | 0.38 | — | — |
| | M 2 | 92.32 | 4.07 | — | — |
| d | M 1 | 99.54 | — | — | — |
| | M 2 | 99.71 | — | — | — |
| e | M 1 | 95.81 | 3.62 | — | — |
| | M 2 | 100.0 | — | — | — |

TABLE 1-continued

| | Autoclave | Tocopherols in the reacted mixture (%) | | | |
|---|---|---|---|---|---|
| | | Alpha | Beta | Gamma | Delta |
| f | M 1 | 100.0 | — | — | — |
| | M 2 | 94.39 | 5.55 | — | — |

The mean conversion into α-tocopherol is 98.3% when triethyl phosphate (M1) is used and 97.5% when $P_2O_5$ (M2) is used.

EXAMPLE 4

For reaction mixture similar to Example 3, test panels of conventional steel grades were additionally introduced into the autoclaves in order to check the corrosion rate of the materials. Each test lasted about 60–70 h.

The following corrosion rates in mm/year were obtained:

| | Steel (DIN No.) | Triethyl phosphate as catalyst | $P_2O_5$ as catalyst |
|---|---|---|---|
| a | 1.4571 | 0.3 | 1.51 |
| b | 1.4539 | 0.03 | 1.27 |
| c | 1.4439 | 0.05 | 1.39 |
| d | 1.4465 | 0.08 | 0.55 |

This Example clearly shows that the steels tested were sufficiently stable to the reaction mixture containing triethyl phosphate, but not resistant to the $P_2O_5$-containing reaction mixture.

We claim:

1. A process for the preparation of d-α-tocopherol from a mixture obtained from natural intermediates and containing α-, β, γ- and δ-tocopherols, by methylation at the aromatic ring of the tocopherols by reaction with formaldehyde or with a compound which donates formaldehyde under the reaction conditions, and subsequent catalytic hydrogenation, wherein the reaction with formaldehyde or with the formaldehyde donor is carried out at from 150° to 200° C. in the presence of an alkyl ester of phosphoric acid or of phosphorous acid.

2. A process as claimed in claim 1, wherein the reaction with formaldehyde or with the formaldehyde donor is carried out in a $_1$–$C_3$-alkanol, methyl acetate or ethyl acetate.

3. A process as claimed in claim 1, wherein the formaldehyde donor used is paraformaldehyde, trioxane or methylal.

4. A process as claimed in claim 1, wherein the reaction with formaldehyde and the catalytic hydrogenation are carried out together in a pressure vessel.

5. A process as claimed in claim 4, wherein a pressure of from 20 to 150 bar is employed.

6. A process as claimed in claim 4, wherein the hydrogenation catalyst used is a noble metal catalyst.

7. A as claimed in claim 1, wherein the reactants are combined at the reaction temperature under hydrogen pressure in a pressure vessel.

* * * * *